US00PP31714P2

(12) United States Plant Patent
Kordes

(10) Patent No.: US PP31,714 P2
(45) Date of Patent: May 5, 2020

(54) MINIATURE ROSE PLANT NAMED 'KORPOT085'

(50) Latin Name: *Rosa hybrida*
Varietal Denomination: KORpot085

(71) Applicant: W. KORDES' SÖHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 16/350,307

(22) Filed: Oct. 31, 2018

(30) Foreign Application Priority Data

Oct. 18, 2018 (QZ) ..... PBR 2018/2620

(51) Int. Cl.
*A01H 5/02* (2018.01)
*A01H 6/74* (2018.01)

(52) U.S. Cl.
USPC ..... Plt./122
CPC ..... *A01H 6/749* (2018.05)

(58) Field of Classification Search
USPC ..... Plt./122
CPC ..... A01H 6/749; A01H 5/02
See application file for complete search history.

(56) References Cited

U.S. PATENT DOCUMENTS

PP23,845 P2 8/2013 Kordes
PP27,221 P3 10/2016 Kordes

*Primary Examiner* — Keith O. Robinson
(74) *Attorney, Agent, or Firm* — Buchanan Ingersoll & Rooney PC

(57) ABSTRACT

A new and distinct variety of miniature rose plant, herein referred to by its cultivar name, 'KORpot085', is provided which forms in abundance on a substantially continuous basis attractive, orange-red colored blossoms. The vegetation is vigorous and the growth habit is compact. Attractive ornamental foliage is formed and good disease resistance is exhibited. The new variety is particularly well suited for providing distinctive ornamentation in the landscape.

1 Drawing Sheet

Botanical/commercial classification:
Latin name—*Rosa hybrida.*
Common name—Miniature Rose Plant.
Varietal denomination: 'KORpot085'.

CROSS-REFERENCE TO RELATED APPLICATIONS

This application claims priority to Plant Breeders' Right Application Number 2018/2620, which was filed at Community Plant Variety Office in the European Union on Oct. 18, 2018, the contents of which are hereby incorporated by reference for all purposes.

SUMMARY OF THE INVENTION

The new variety of *Rosa hybrida* Miniature Rose Plant of the present invention was created during 2014 at Offenseth-Sparrieshoop, Germany by artificial pollination wherein two parents were crossed which previously had been studied in the hope that they would contribute the desired characteristics. The female parent (i.e., seed parent) of the new variety was the 'KORpot040' variety (U.S. Plant Pat. No. 27,221). The male parent (i.e., pollen parent) of the new variety was an unnamed seedling (non-patented) from the cross of an unnamed seedling and the 'KORelamur' variety (not patented).

The parentage can be summarized as follows:

'KORpot040' x (unnamed seedling x 'KORelamur')

The seeds resulting from the above pollination were sown and small plants were obtained which were physically and biologically different from each other. Selective study resulted in the identification of a single plant of the new variety.

It was found that the new miniature rose plant of the present invention possesses the following combination of characteristics:

(a) abundantly and substantially continuously forms attractive, orange-red colored blossoms,
(b) exhibits a compact growth habit,
(c) forms vigorous vegetation,
(d) forms attractive ornamental foliage, and
(e) exhibits good disease resistance.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the 'KORpot040' variety (i.e., seed parent) exhibits red colored flowers and forms clusters of flowers, whereas the new variety exhibits orange-red colored flower, forms solitary flowers, and exhibits a larger growth habit compared to the 'KORpot040' variety. Additionally, the unnamed seedling from the cross of (unnamed seedling x 'KORelamur') (i.e., pollen parent) exhibits red colored flowers, a smaller flower size, and a smaller growth habit than the new variety. Moreover, the new variety can be readily distinguished from non-parental related similar varieties. For example, the 'KORbailand' (U.S. Plant Pat. No. 23,845) variety exhibits smaller sized flowers and less petals compared to the new variety. In addition, the 'KORbailand' provides no noticeable fragrance, whereas the new variety provides a slight fragrance.

The new variety has been found to undergo asexual propagation in Klein Offenseth-Sparrieshoop, Germany by a number of routes, such as vegetative cuttings. Asexual propagation techniques in Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot085'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Marslev, Denmark while growing indoors on its own roots in 10.5 cm containers.

FIG. 1—illustrates a specimen of a plant displaying floral buds and flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during March, while growing in a one-gallon container on its own roots in a greenhouse at Cochranville, Pa.

Class: Miniature Rose Plant.

Plant:

*Habit*.—Very bushy, compact, and upright.

*Height*.—Approximately 35.0 cm on average.

*Width*.—Approximately 32.0 cm on average.

Branches:

*Stem color*.—Commonly near Green Group 138A.

*Stem length*.—Approximately 35.0 cm on average.

*Surface texture*.—Smooth.

*Thorns*.—Number of thorns per area of stem: approximately 4 thorns per 6.0 cm of stem length, on average. — young thorns: few to moderate amount; length is approximately 2.0 mm on average, width is approximately 2.0 mm at point of attachment on average, and color is commonly near Greyed-Purple Group 185C. — old thorns: few to moderate amount; length is approximately 3.0 mm on average, width is approximately 3.0 mm at point of attachment on average, and color is commonly near Grey Group 201A.

Foliage:

*General appearance*.—Ornamental.

*Young foliage*.—Upper surface color: commonly near Green Group 137A. — under surface color: commonly near Greyed-Green Group 191A.

*Old foliage*.—Upper surface color: commonly near Green Group 137A. — under surface color: commonly near Green Group 138B.

*Petioles*.—Upper surface: texture is smooth, color is commonly near Green Group 137B with some Greyed-Red Group 178A at the center. — under surface: texture is smooth, color is commonly near Yellow-Green Group 144C. — length: approximately 1.3 cm on average.

*Rachis*.—Color: upper surface is commonly Green Group 137B, under surface is commonly near Yellow-Green Group 144C. — size: length is approximately 4.5 cm on average. — surface texture: upper surface is smooth; under surface is smooth with some small prickles.

*Stipules*.—Length: approximately 5.0 mm on average. — width: approximately 4.0 mm on average. — margin: entire to erose. — color: upper surface is commonly near Yellow-Green Group 146B; under surface is commonly near Yellow-Green Group 146C.

*Leaf margin*.—Serrate.

Leaflets:

*Number*.—3, 5, and 7.

*Arrangement*.—Odd pinnate.

*Shape*.—Ovate.

*Venation*.—Pattern is reticulate.

*Texture*.—Upper surface is smooth; under surface is smooth.

*Size*.—Terminal leaflet: length is approximately 4.0 cm on average; width is approximately 2.5 cm on average; margin undulation is absent; glossiness intensity on the upper surface is moderate; apex shape is acute; and base shape is rounded. — lower leaflets: length is approximately 2.0 cm on average and width is approximately 1.5 cm on average. — 5-Leaflet leaf: length is approximately 8.0 cm on average and width is approximately 5.0 cm on average.

Inflorescence:

*Number of flowers*.—Approximately 14 open blooms on average on a plant at once.

*Number of blooms per stem*.—Commonly between 1 and 2 blooms per stem on average.

*Type*.—Solitary.

*Peduncle*.—Color: commonly Yellow-Green Group 144A. — diameter: approximately 3.0 mm on average. — length: approximately 4.0 cm on average. — surface texture: sparely glandular.

*Sepals*.—Number commonly 5. — upper surface color and texture: covered in short pubescence and color is commonly near Yellow-Green Group 144A. — under surface color and texture: puberulent and color is commonly near Yellow-Green Group 144B. — size: length is approximately 1.5 cm on average and width is approximately 1.0 cm on average. — shape: lanceolate; apex is acute to aristate. — margin: entire with occasional extensions on one or two sepals measuring approximately 5.0 mm in length and approximately 1.0 mm in width.

*Bud*.—Shape: ovoid. — size: length is approximately 2.0 cm on average; width is approximately 1.3 cm on average. — color (when opening): commonly near Red Group 45B.

*Flower*.—Orange-red colored. — solitary flowers formed. — form: double, flat to cuplike. — shape:

star shaped. — diameter: approximately 5.5 cm on average. — height: approximately 2.0 cm on average. — duration: commonly on the plant approximately 25 to 30 days on average. — petal color when first and fully open: upper and under surfaces are commonly between near Red Group 42B and Red Group 42C with a small basal spot of between near Yellow Group 8B to Yellow Group 8D. — petal color when fading: upper and under surfaces are commonly near Red Group 43C with a small basal spot of near Yellow Group 8D. — basal spot size: approximately ¼ the length of the petal on average.

*Fragrance*.—Slight fragrance, which is light, sweet and floral.

*Petal*.—Number: approximately 46 on average. — drop: good. — length: 1.6 cm on average. — width: 2.6 cm on average. — shape: overall shape is broadly obovate; apex is round; and base is cuneate. — margin: entire. — margin undulation of petal: moderate. — texture: upper and under surface is glabrous.

*Petaloids*.—Number: approximately 3 to 5 on average. — color: upper and under surfaces are commonly near Red Group 42B with a basal spot of near Yellow Group 8B.

*Stamen*.—Number approximately 92 on average. — anthers: number is about 92 and color is commonly near Red Group 48A; and length is approximately 6.0 mm on average. — filaments: length is approximately 4.0 mm on average and color is commonly near Yellow Group 10B.

*Pistils*.—Arrangement: separate and free. — number: approximately 50 on average. — style: color is commonly near Yellow-Green Group 150C and length is approximately 1.0 cm on average. — stigma: color is commonly near Yellow-Orange Group 16B and diameter is typically less than 1.0 mm.

*Receptacle*.—Achenes stand on the bottom and wall; diameter is approximately 8.0 mm on average, shape is oval, color is commonly near Yellow-Green Group 144A, and surface texture is smooth.

*Pollen*.—None observed.

*Hips/seed*.—None observed.

Development:

*Vegetation*.—Vigorous and strong.

*Blooming*.—Abundant and substantially continuous.

*Winter hardiness*.—Unknown.

*Resistance to disease*.—Good resistance to Powdery mildew (*Sphaerotheca pannosa*) and *Botrytis* (*Botrytis cinerea*) disease under normal greenhouse growing conditions in Cochranville, Pa.

Plants of the 'KORpot085' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) abundantly and substantially continuously forms attractive, orange-red colored blossoms, (b) exhibits a compact growth habit, (c) forms vigorous vegetation, (d) forms attractive ornamental foliage, and (e) exhibits good disease resistance;

substantially as herein shown and described.

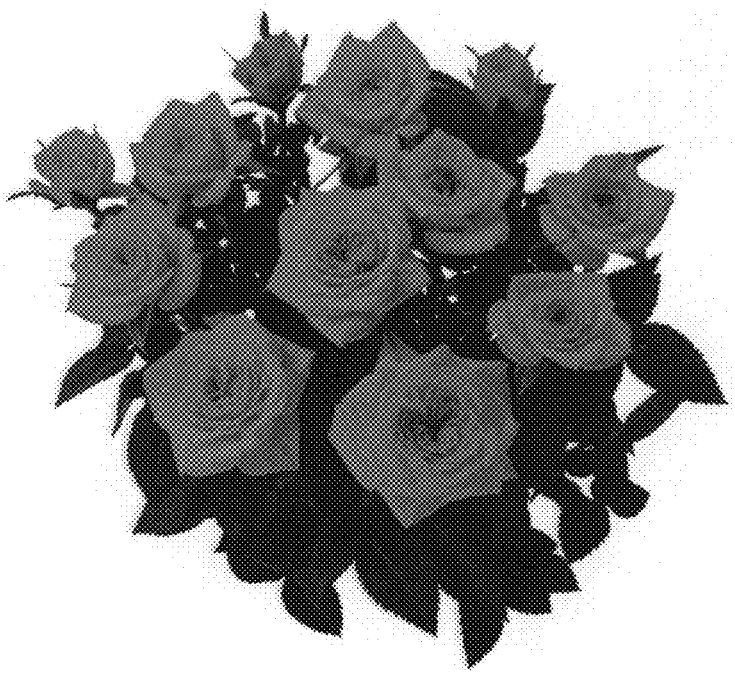

* * * * *